(12) United States Patent  
Hassonjee et al.

(10) Patent No.: US 7,308,294 B2  
(45) Date of Patent: Dec. 11, 2007

(54) TEXTILE-BASED ELECTRODE SYSTEM

(75) Inventors: Qaizar N. Hassonjee, Chadds Ford, PA (US); Juan Cera, Middletown, DE (US); Robert-Michael Bartecki, Neweak, DE (US); Thomas A. Micka, West Grove, PA (US); Claudia Schultze, Greenville, DE (US); Stacey B. Burr, West Lafayette, IN (US); Eleni Karayianni, Geneva (CH)

(73) Assignee: Textronics Inc., Wilmington, DE (US)

( * ) Notice: Subject to any disclaimer, the term of this patent is extended or adjusted under 35 U.S.C. 154(b) by 363 days.

(21) Appl. No.: 11/082,240

(22) Filed: Mar. 16, 2005

(65) Prior Publication Data

US 2006/0211934 A1  Sep. 21, 2006

(51) Int. Cl.  
*A61B 5/04* (2006.01)

(52) U.S. Cl. .................. 600/386; 600/388; 600/389; 600/390; 600/395

(58) Field of Classification Search ................ 600/372, 600/388, 395  
See application file for complete search history.

(56) References Cited

U.S. PATENT DOCUMENTS

| | | |
|---|---|---|
| 3,826,246 A | 7/1974 | Raddi et al. |
| 4,120,294 A | 10/1978 | Wolfe |
| 4,160,711 A | 7/1979 | Nishizawa et al. |
| 4,239,046 A | 12/1980 | Ong |
| 4,554,923 A | 11/1985 | Batters |
| 4,572,960 A | 2/1986 | Ebneth et al. |
| 4,583,547 A | 4/1986 | Granek et al. |
| 4,664,118 A | 5/1987 | Batters |
| 4,809,700 A | 3/1989 | Castelli et al. |
| 4,911,169 A | 3/1990 | Ferrari |
| 5,103,504 A | 4/1992 | Dordevic |
| 5,275,861 A | 1/1994 | Vaughn |
| 5,289,824 A | 3/1994 | Mills et al. |
| 5,317,269 A | 5/1994 | Mills et al. |
| 5,365,935 A | 11/1994 | Righter et al. |
| 5,374,283 A | 12/1994 | Flick |
| 5,467,773 A | 11/1995 | Bergelson et al. |

(Continued)

FOREIGN PATENT DOCUMENTS

CA  2428884  5/2002

(Continued)

OTHER PUBLICATIONS

G. Troster, "The Agenda of Wearable Healthcare," IMIA Yearbook of Medical Informatics 2005: Ubiquitons Health Care Systems, Hauz R., Kullkouskim C., eds. Stuttgart 2004 pp. 125-138.

(Continued)

*Primary Examiner*—Lee S. Cohen  
(74) *Attorney, Agent, or Firm*—Connolly Bove Lodge & Hutz LLP

(57) ABSTRACT

Textile-based electrodes include a fabric portion having stretch-recovery non-conductive yarns and an electrically conductive region having stretch-recovery electrically conductive yarn filaments. The electrodes can further include float yarns and can be configured in a textured or ribbed construction. When incorporated into a garment, the electrodes can be used to monitor biophysical characteristics, such as the garment wearer's heart rate.

16 Claims, 9 Drawing Sheets

U.S. PATENT DOCUMENTS

| | | |
|---|---|---|
| 5,503,887 A | 4/1996 | Diaz et al. |
| 5,586,556 A | 12/1996 | Spivey et al. |
| 5,771,027 A | 6/1998 | Marks et al. |
| 5,906,004 A | 5/1999 | Lebby et al. |
| 5,968,854 A | 10/1999 | Akopian et al. |
| 6,145,551 A | 11/2000 | Jayaraman et al. |
| 6,210,771 B1 | 4/2001 | Post et al. |
| 6,356,238 B1 | 3/2002 | Gainor et al. |
| 6,377,216 B1 | 4/2002 | Cheadle et al. |
| 6,381,482 B1 | 4/2002 | Jayaraman et al. |
| 6,399,879 B1 | 6/2002 | Ueda et al. |
| 6,677,917 B2 | 1/2004 | Van Heerden et al. |
| 6,680,707 B2 | 1/2004 | Allen et al. |
| 6,738,265 B1 | 5/2004 | Svarfvar et al. |
| 6,748,260 B2 | 6/2004 | Au et al. |
| 6,788,978 B2 | 9/2004 | Vesnaver |
| 6,970,731 B1 | 11/2005 | Jayaraman et al. |
| 2003/0224681 A1 | 12/2003 | Koch |
| 2004/0023576 A1 | 2/2004 | Rock et al. |
| 2004/0215089 A1 | 10/2004 | Bergelson et al. |
| 2004/0235381 A1 | 11/2004 | Iwasaki et al. |
| 2006/0183990 A1 | 8/2006 | Tolvanen |

FOREIGN PATENT DOCUMENTS

| | | |
|---|---|---|
| EP | 1 319 741 | 6/2003 |
| FR | 2 745 690 | 9/1997 |
| GB | 1467344 | 3/1977 |
| WO | WO-92/13352 | 8/1992 |
| WO | WO-01/02052 A2 | 1/2001 |
| WO | WO-01/37366 A1 | 5/2001 |
| WO | WO-01/39326 A1 | 5/2001 |
| WO | WO-02/071935 A1 | 9/2002 |
| WO | WO-03/094717 A1 | 11/2003 |
| WO | WO-2004/006700 A1 | 1/2004 |
| WO | WO-2004/058346 A1 | 7/2004 |
| WO | WO-2005032366 | 4/2005 |

OTHER PUBLICATIONS

A.M. Albisser, et al., "Atraumatic electrodes for cardiac monitoring," Journal of Association for the Advancement of Medical Instrumentation, vol. 5, No. 2, Apr. 1971.

Carla Hertieer, et al., "Intelligent Textiles for Children in a Hospital Environment," 2nd Autex Conference, Jul. 2002, pp. 44-48.

Scilingo E.P., et al., "Performance Evaluation of Sensing Fabrics for Monitoring Physiological and Biomechanical Variables," IEEE Transactions on Information Technology in Biomedicine, vol. 9, No. 3, Sep. 2005, pp. 345-352.

Krzysztof Gniotek, et al., "The Basic Problems of Textronics," Fibres & Textiles, Jan./Mar. 2004, vol. 12, No. 1 (45), pp. 13-16.

TEXTILE-BASED ELECTRODE SYSTEM

FIELD OF THE INVENTION

The invention relates to a textile-based electrode or electrode system that can be used in the form of a wearable article. The wearable article can be, for example, adapted for biophysiological monitoring using textile-based electrodes to receive biophysiological signals from the wearer.

BACKGROUND OF THE INVENTION

Textile-based electrodes consisting of electrically conductive wires surrounded by a region of electrically nonconductive textile fibers can be integrated with a wearable article, such as a garment. The wearable article can be adapted to receive or transmit electrical impulses to or from the wearer and, in turn, to or from an electrical device. The patent document WO 01/02052, assigned to Bekaert, discloses such a wearable article.

Wearable textile-based sensors for sensing or otherwise reporting the heart rate (the pulse) of the wearer are disclosed in patent document WO 02/071935, assigned to RTO Holding OY.

Patent document WO 03/094717, assigned to Koninklijke Philips Electronics NV, discloses a textile article that is provided with a region of skin contacting electrodes that are fully integrated within a textile article. The disclosed textile article takes the form of a "bra or a ladies top," which is otherwise electrically nonconducting. The article is provided with partially overlapping layers of electrically conductive material and electrically insulative material arranged to partially cover and electrically isolate the electrically conductive material.

Patent document WO 2004/006700, assigned to Tefron Ltd., discloses a circularly knit garment having an inner surface electrically-conductive region disposed close to the wearer's skin. The inner electrically-conductive region cooperates to conduct electrical signals to an outerlying electrically-conductive region. Such electrical signals may include the heart rate coming from the wearer or an electrostimulation means going to the wearer.

Each of these patent documents relates an objective to provide an electrically-conductive region, which can function as an electrode integrated with a garment, a belt, or other wearable article of traditional textile construction. Generally, these patent documents disclose an electrically-conductive region that is otherwise electrically isolated from the remainder of the garment or wearable. Furthermore, these patent documents disclose placing at least one electrically-conductive region of the garment in close contact with the skin of the wearer. As a result, the electrode, formed by this electrically-conductive region in contact with the skin, provides a pick-up point for electrical signals generated within the corpus of the wearer. Alternatively, such an electrode provides a point of contact on the skin to receive an electrical signal generated externally to the wearer. In summary, these patent documents provide means to communicate electrical signals to or from the corpus of a garment wearer.

In addition, these patent documents also generally disclose at least a second textile electrode. More often, the second electrode is integrated with the garment and located at or near an exterior surface of the garment. The second electrode can also be advantageously placed overlying the electrode in skin contact, while also having a portion of the garment's electrically insulating materials of construction therebetween. Where an electrical connection between the electrode(s) in skin contact and the exterior electrode(s) is desired, such connection can be established using metallic wires. Alternatively, the skin contact electrode can be folded over in such a manner as to form the exterior surface electrode continuously.

Where an electrical connection between a garment-integrated electrode in skin contact with the wearer and a garment-integrated exterior electrode is established using metallic wires, certain limitations may exist. Such limitations can be present, for example, when biophysical monitoring via electrical contact with the corpus is desired. These limitations, for example, may include the difficulty of making metallic wires part of a traditionally fabricated textile due to the fragility and durable flexibility of metal wires.

Similarly, other configurations may suffer certain limitations. For example, configurations incorporating "folded over" and partially overlapping layers of electrically conductive material (with electrically insulative material arranged to electrically isolate the electrically conductive material) may severely limit the freedom to design the placement of electrodes integrated with a garment or textile article.

Accordingly, there exists a need to provide a textile-based electrode capable of overcoming one or more of the deficiencies of the prior art.

SUMMARY OF THE INVENTION

The present invention provides a textile-based electrode or electrode system that can be incorporated in to a wearable article, such as a garment. The textile-based electrode can include a fabric portion having stretch-recovery non-conductive yarns and an electrically conductive region having stretch-recovery electrically conductive yarn filaments.

The textile-based electrode system can include first and second fabric portions that include electrically conductive regions. The electrically conductive regions can be disposed in a partially overlapping relationship, allowing for a region of partial physical contact that can result in electrical conduction between the electrically conductive regions.

At least one of the electrically conductive regions can include a float yarn. In addition, at least one of the electrically conductive regions can be made up of an elastified electrically conductive yarn and/or an elastic yarn at least partially plated with a conductive yarn. In one embodiment, the electrically conductive regions can include a fabric having a textured or ribbed construction. In further embodiments, the electrically conductive regions can include a portion or portions having at least one hydrophobic material and/or can be separated by a region having at least one hydrophobic material.

Textile-based electrodes falling within the scope of the present invention can be connected to a measuring device. The measuring device can, for example, be used to monitor biophysical signals of a wearer of a garment incorporating the electrodes. For instance, in one embodiment, the textile-based electrodes can be used to facilitate monitoring a wearer's heart rate.

BRIEF DESCRIPTIONS OF THE DRAWINGS

The present invention will be described in the following detailed description with reference to the following drawings.

DETAILED DESCRIPTION OF THE INVENTION

Figure 1A:
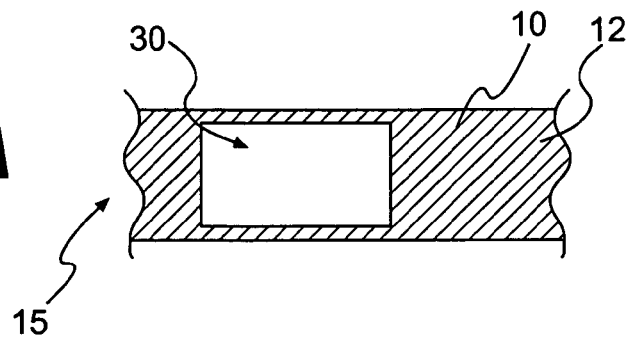
FIGS. 1A and 1B are schematic representations of a top plain view and a bottom plain view of a first textile-based electrode.

The present invention, in one embodiment, can provide a textile-based electrode capable of being fully integrated with a wearable article that can be adapted to allow contact of the electrode with the corpus of the wearer. The textile-based electrode disclosed herein is capable of being adapted for the transmission of electrical signals to the wearer of an article integrated with the electrode. For example, such textile-based electrode may be adapted for the biophysiological monitoring of the wearer.

The textile-based electrode disclosed herein is also capable of transmitting or receiving electrical signals via contact with the corpus of the wearer without relying on fragile connection wires. The textile-based electrode may also be specifically adapted for the reliable contact with corpus of the wearer, further providing relatively consistent electrical continuity with a complementary textile-based electrode (i.e., without signal loss or short circuiting while the wearer moves freely). In this regard, the textile-based electrode may be stretchable in the electrically conductive area due to the presence of elastic materials that are knitted or woven with electrically conductive yarns or filaments and/or through the use of yarns or filaments that are both elastic and electrically conductive.

In one embodiment, the textile-based electrode can be included within an electrode system comprising a first fabric portion provided with a portion of electrically conductive yarns in a knit construction. The knit construction can, for example, be chosen from among single jersey, ribbed knit, mock ribbed knit, and ribbed knit 1×1 and 1×3 constructions. The portion of electrically conductive yarns can be surrounded by, and electrically isolated from, the first fabric portion.

The textile-based electrode can exhibit stretchability in the electrically conductive area due to the presence of a material, such as Lycra® spandex, plated with a conductive yarn or filament. The textile-based electrode can also exhibit stretchability in the electrically conductive area through the use of a conductive yarn, such as the conductive yarns disclosed in WO 2004/097089A1 (assigned INVISTA Technologies S. á. r. I.), the entire disclosure of which is incorporated herein by reference. In addition, the textile-based electrode can exhibit stretchability by using different types of knit constructions, such as a ribbed construction (including, for example, 1×1 or 1×3 ribbed knit constructions).

In a further embodiment, a textile-based electrode is provided within an electrode system, which comprises at least a first fabric portion and a second fabric portion disposed in a partially overlying relationship. The first fabric portion may comprise at least a first electrically conductive region (a first "electrode") and the second fabric portion may comprise at least a second electrically conductive region (a second "electrode"). The electrically conductive region of the first fabric portion and the electrically conductive region of the second fabric portion can cooperate to provide a region of partial physical contact. This physical contact region can thereby establish electrical conduction between the first and second "electrodes."

The first and second electrically conductive regions or "electrodes" each comprise at least a portion of electrically conductive yarns. In addition, the first and second electrically conductive regions or "electrodes" may each further comprise at least a portion of "float yarns."

Embodiments falling within the scope of the present invention may be further described with reference to the figures disclosed herein.

Figure 1B:
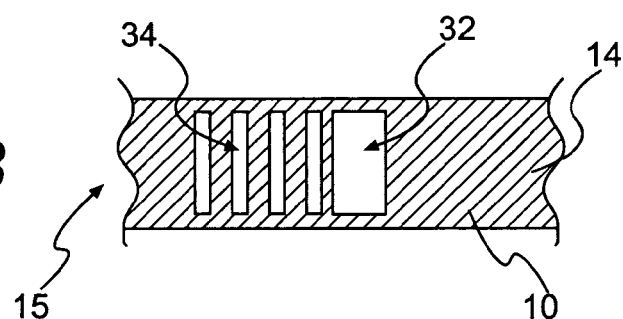

In one embodiment, a first textile-based electrode is provided within an electrode system comprising a first fabric portion 10 that is provided with a portion of electrically conductive yarn 30, as represented in FIGS. 1A and 1B. In this embodiment, the portion of electrically conductive yarn 30 (FIG. 1A) is surrounded by and electrically isolated from the first fabric portion 10.

Figure 1C:
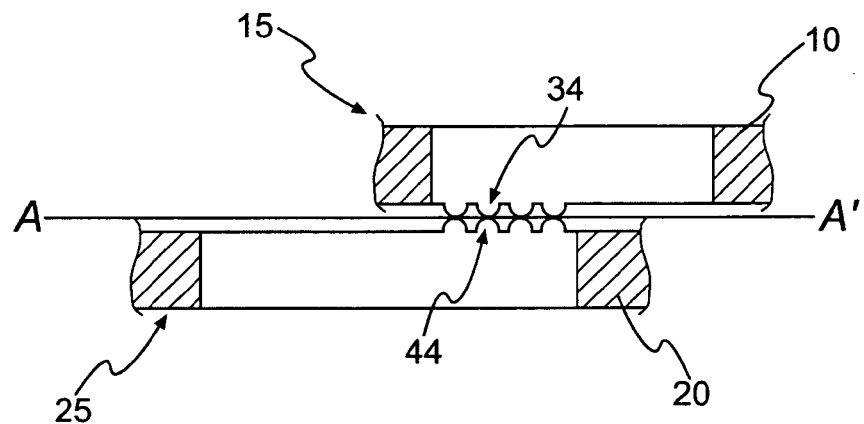
FIG. 1C is a schematic representation in side elevation of the first textile-based electrode of FIGS. 1A and 1B, comprising a portion of electrically conductive float yarns in contact with a portion of electrically conductive float yarns of a second textile-based electrode of FIGS. 1D and 1E.
Figure 1D:
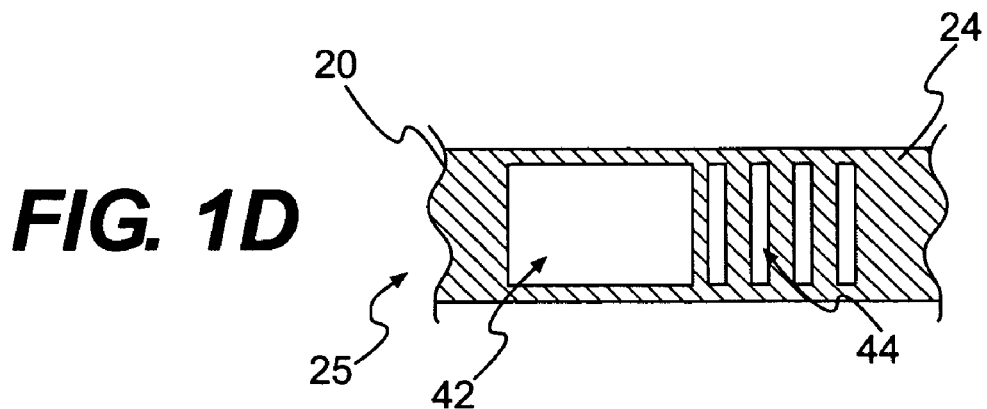
FIGS. 1D and 1E are schematic representations of a top plain view and a bottom plain view of a second textile-based electrode.
Figure 1E:
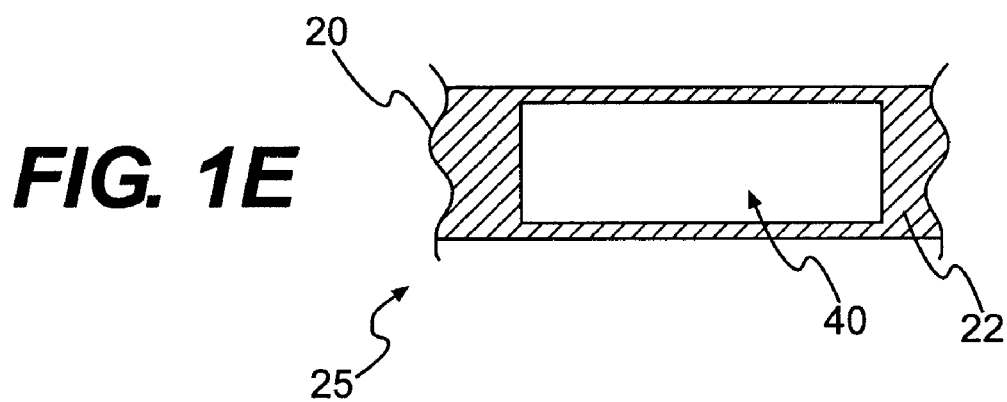

A second textile-based electrode comprises a first fabric portion 20 that is provided with a portion of electrically conductive yarns 40, as represented in FIGS. 1D and 1E.

In embodiments falling within the scope of the invention, a knit construction can be used. The knit construction may, for example, be chosen from among single jersey, mock ribbed knit, and ribbed knit 1×1 and 1×3 constructions for both the fabric portion 10 and 20 and the conductive yarns 30 and 40. As is known to a person having skill in the art, in such knit fabrics, the wales, or vertical rows of stitches, typically intermesh alternately on the face (odd number wales) and on the back (even number wales) of the fabric. Rib-knit fabrics of this type have been shown to have good elasticity in the length and width directions and can provide good body form fitting garments.

A further embodiment of the invention provides for the conductive yarns 30 and 40 to be knitted in with floats. Floats, as known to a person having skill in the art, comprise a portion of yarn that extends over the fabric without being knitted in (i.e. floating or lying on the fabric surface). Fabric portions 10 and 20 with electrically conductive yarns 30 and 40 in a rib-knit construction can provide a textile-electrode structure wherein yarns 30 and 40 are floated over the ribbed structure of the fabric. As a result, these conductive float yarns 34 and 44 (FIGS. 1A, 1B, 1D, and 1E) are readily accessible on the surface of the fabric. The ready accessibility of the conductive float yarns 34 and 44 facilitates electrical contact between the conductive yarn portions of fabric through the physical contact of the float yarns. In one embodiment, the electrical contact between conductive yarn portions may be further facilitated by stitching conductive float yarns 34 and 44 together.

As shown in FIG. 1C, the first textile-based electrode 15 and the second textile-based electrode 25 may be placed adjacent to one another, putting float yarns 34 and 44 in contact with one another to establish electrical conductive contact.

Materials suitable for use as conductive yarns 30 and 40, and thus the float yarns 34 and 44, include, for example, those yarns disclosed in patent document WO 2004/097089A1 (assigned to the applicant INVISTA Technologies S. á. r. l.), the entire disclosure of which is incorporated herein by reference. The conductive yarns disclosed within WO 2004/097089A1 (hereinafter called ETG1 yarns) can inherently provide elastic stretch and recovery and can lend themselves to knit constructions for embodiments disclosed herein. Inelastic conductive filaments suitable for preparing the elastic conductive yarns according to the disclosures in WO 2004/097089A1 include those yarns from BEKAERT Fibre Technologies (such as CONDUFIL® 80 dtex and 24 filament yarns) and those yarns known as Xstatic® yarns of a silver metallized nylon yarn from Laird Sauquoit Industries (Scranton, Pa., U.S.A. 18505).

Electrically nonconductive yarns or traditional textile yarns can be advantageously employed for the bulk of the fabric portion. These yarns can include, for example, cotton, cellulosics, silk, ramie, polyester, and/or nylon. The bulk of the fabric portion can also include combinations of polyester and nylon with elastic yarns (such as LYCRA® branded spandex from INVISTA™ S. á. r. l.).

Figure 1F:
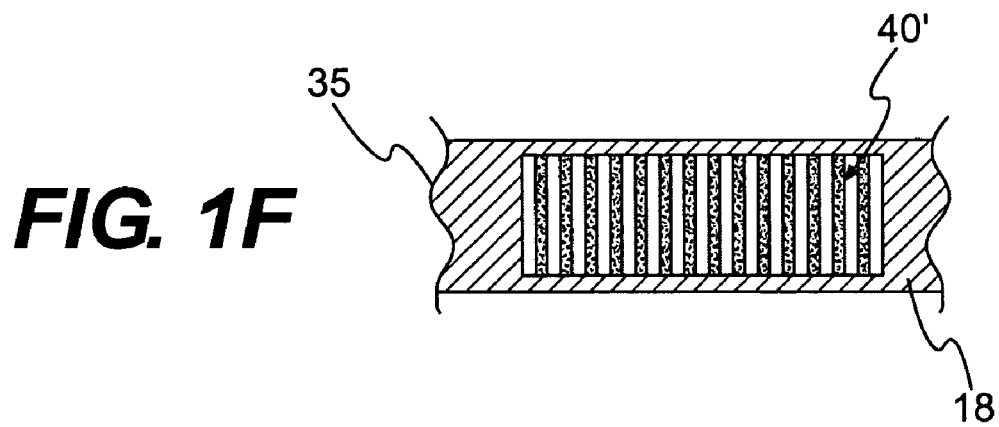
FIG. 1F is a schematic representation of an integrated textile electrode comprising a portion of electrically conductive region using different types of knit construction.

In this regard, FIG. 1F shows a representation of an integrated textile electrode 35 having a portion of an electrically conductive region 40' using different types of knit construction, including a ribbed construction (i.e. 1×1 or 1×3 rib). Such electrode can be within a larger region 18 surrounding the electrically conductive region 40' and having, for example, a ribbed construction. The electrode area can stretch due to, for example, the presence of Lycra® spandex plated with the conductive yarns, or through the use of an elastic conductive yarn, such as a yarn disclosed in WO 2004/097089A1 (ETG1). In addition, through the use of a ribbed construction and elastic materials, the stretch electrode can provide improved contact with the skin and hence better signal pick-up.

Such ribbed construction stretch electrodes can be made, for example, on a SMA-8-TOP1 seamless, 13 inch body size, knitting machine from SANTONI (from GRUPPO LONATI, Italy).

Examples of conductive yarns that can be used in such integrated textile electrodes include Xstatic® 70 denier 2 ply (e.g. silver metallized nylon yarn of 70 denier and 34 filaments from Laird Sauquoit Industries (Scranton, Pa., U.S.A. 18505) and ETG1 yarns (hollow spindle double covered 70 denier nylon yarn on LYCRA® Type 162 "clear " and 20 micron silver plated copper wire from Elektro Feindraht).

FIG. 1C shows an edgewise view of fabric portion 10 and fabric portion 20 oriented about the axis extending from A to A'. As shown in this figure, physical contact can occur between yarn floats 34 in fabric 10 and yarn floats 44 in fabric 20. This physical contact of floats 34 and 44, or a plurality of similar floats, can provide electrical continuity between the fabric portions 10 and 20.

As represented in FIG. 1C, when the conductive float yarn portion 34 of fabric portion 10 is in contact with the conductive float yarn portion 44 of fabric portion 20, the conduction of an electrical signal between the two conductive yarn portions, i.e. from conductive portion 30 on surface 12 to conductive portion 40 on surface 22, can be enabled.

Figure 2A:
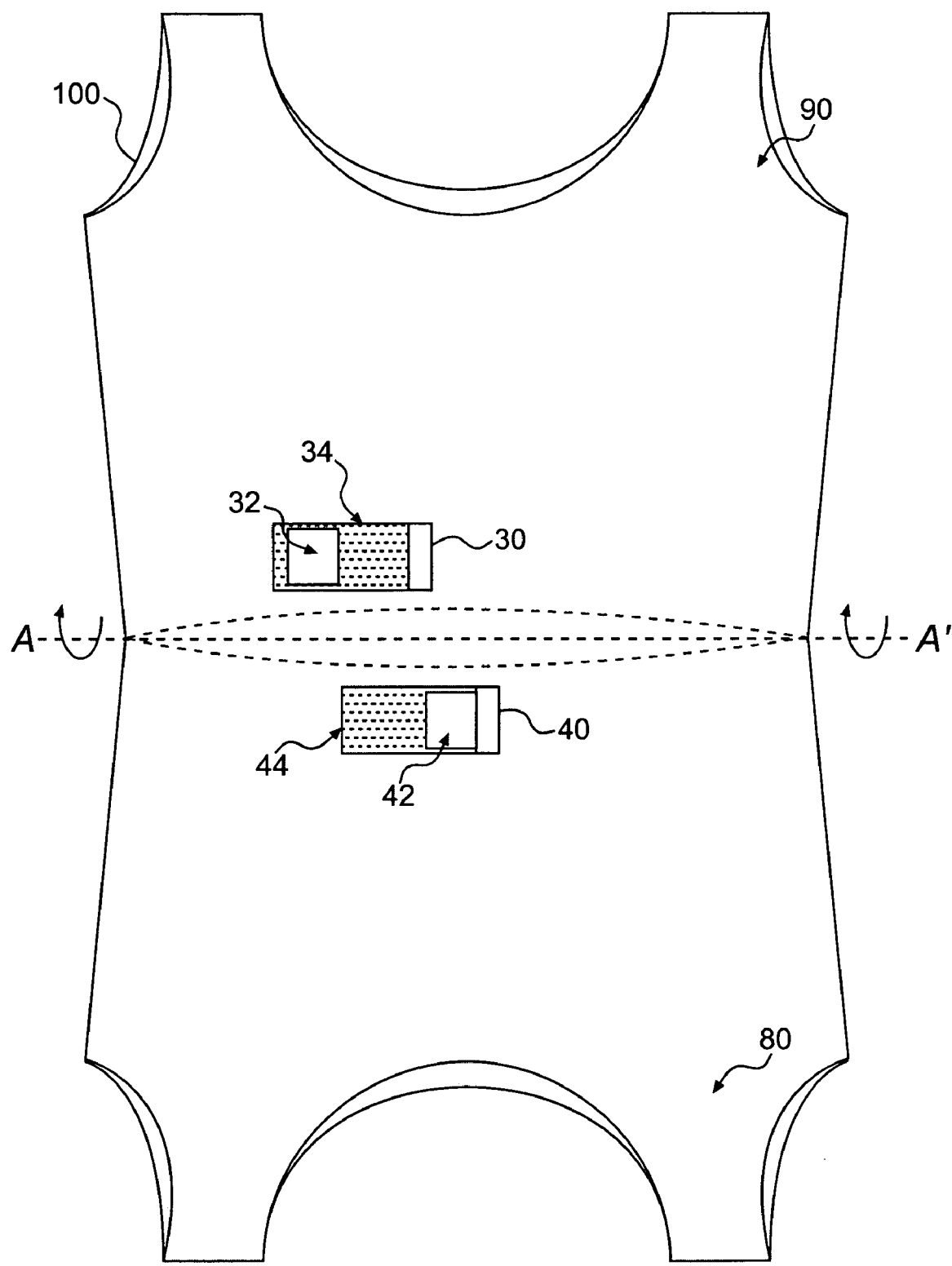
FIGS. 2A and 2B are schematic representations of an upper body wearable article having textile-based electrodes.
Figure 2B:
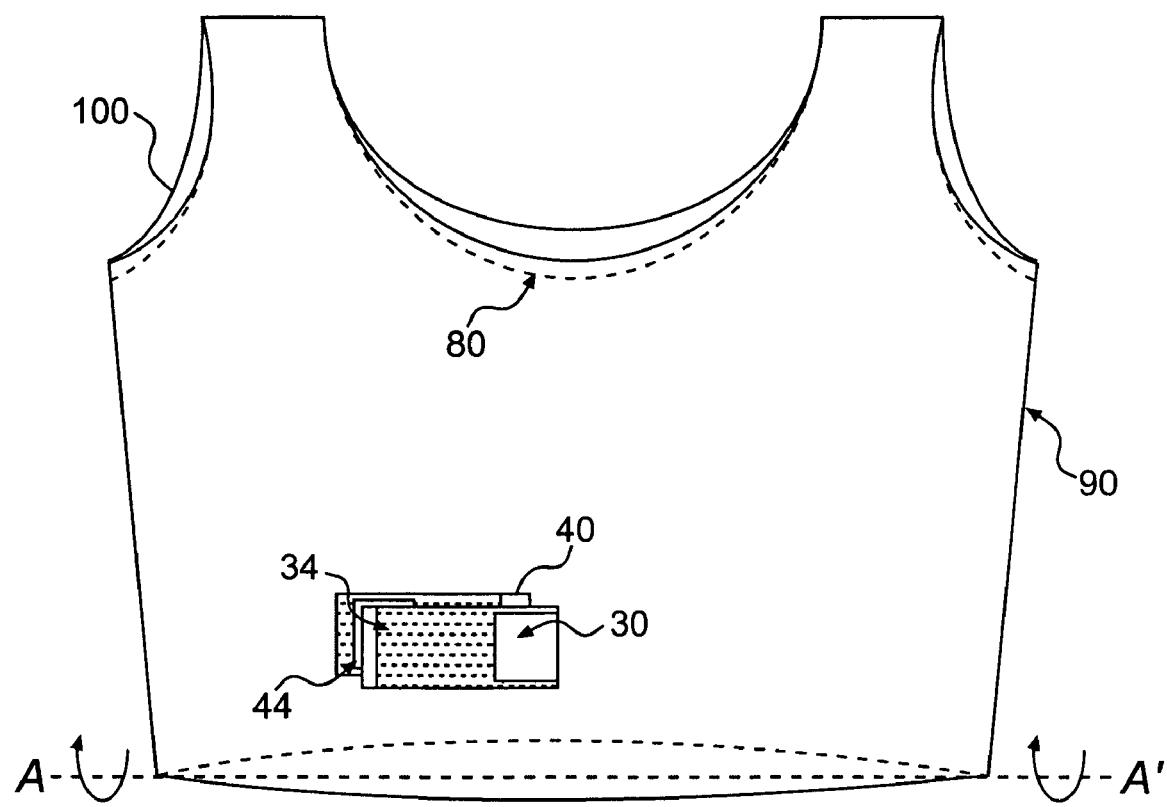

An embodiment of a textile-based electrode system, fully integrated with a wearable article, such as a shirt, is represented with the aid of FIGS. 2A and 2B. In these figures, a wearable 100 is represented as an upper body worn garment. The wearable 100 can be constructed using commonly practiced seamless (circular) knitting technology. In an "as-knitted" form using, for example, seamless technology, wearable 100 takes the shape of a tube with upper 90 and lower 80 mirror image portions about axis-AA'. The lower portion 80 in FIG. 2A, may be folded into the upper portion 90, to form a two ply garment having inner and outer portions, as represented in FIG. 2B. A waist band of a garment can be constructed in a similar manner.

FIGS. 2A and 2B represent wearable 100 as having a textile-based electrode system of the invention fully integrated with it. The outer surface portion of the textile-based electrode system 40, is shown as being associated with lower portion 80. The outer surface portion of the textile-based electrode system 40 is electrically continuous with inner surface portions 42 and with float yarns 44, shown with dashed lines. The outer surface portion of the textile-based electrode system 30, is shown as being associated with upper portion 90 and is electrically continuous with inner surface portions 32 and with float yarns 34, shown with dashed lines. When lower portion 80 is folded into upper portion 90 of wearable 100, float yarn portions 34 and 44 come into physical contact, as shown in FIG. 2B (in the manner as represented by FIG. 1C). As a result of the physical contact between portions 34 and 44, an electrical signal can pass in either direction from electrode 30 on the outer surface of the two ply garment 100, to electrode 40 on the inner surface and thereon to the skin of the wearer.

Figure 3A:
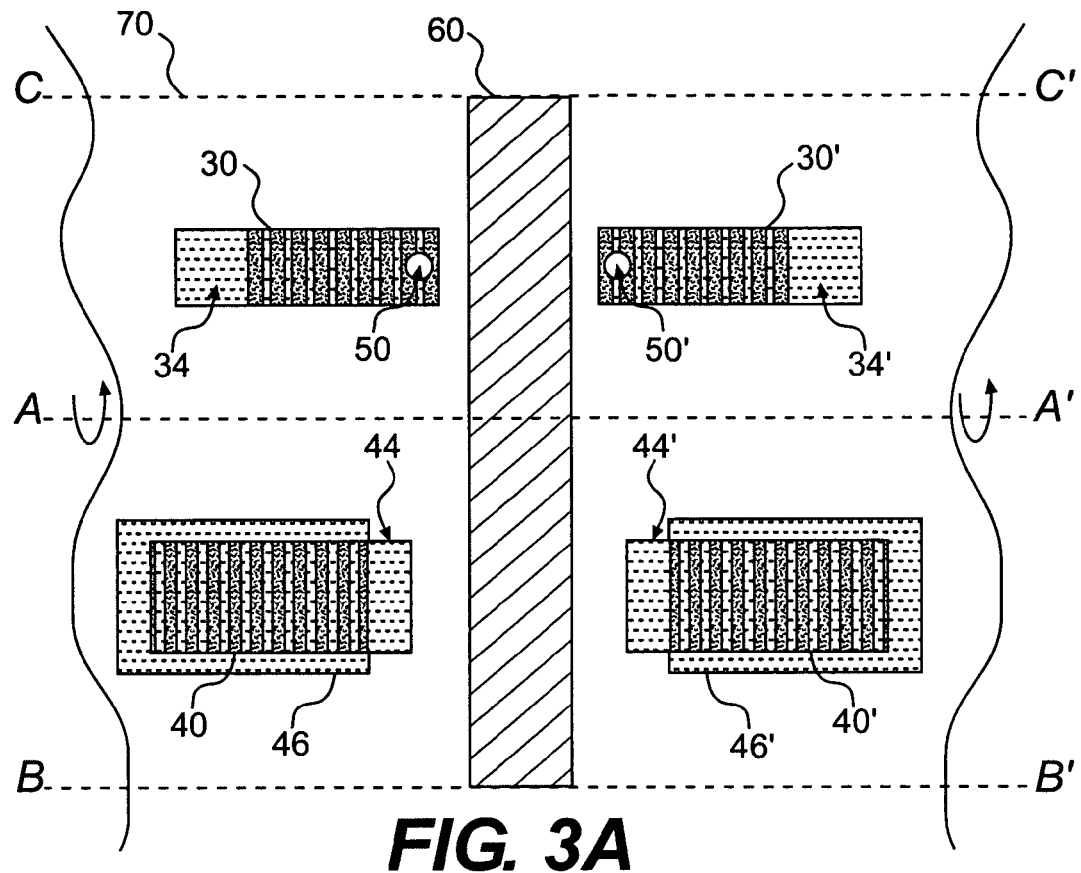
FIG. 3A is a schematic representation in front plain view of textile-based electrodes.
Figure 3B:
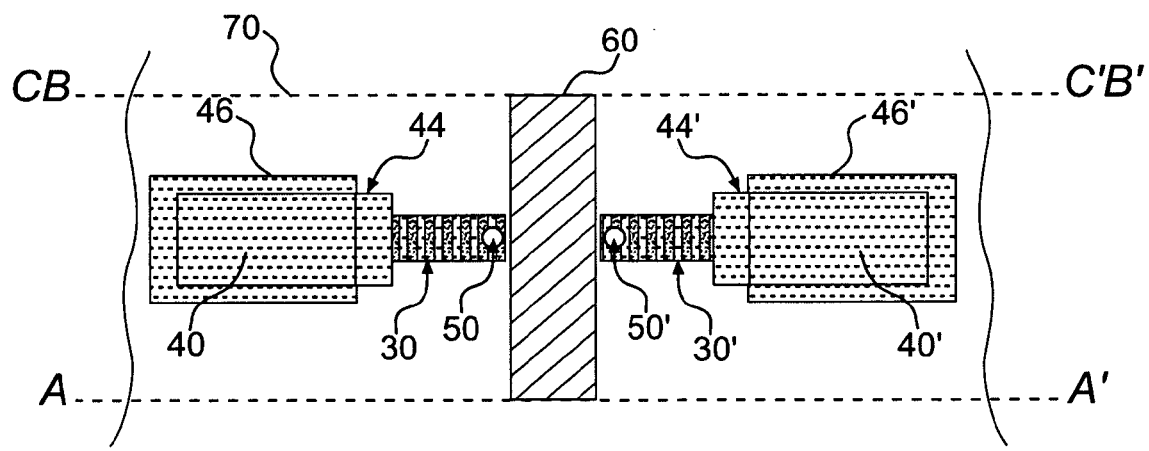
FIGS. 3B and 3C are schematic representations of the textile-based electrodes in folded configuration.

Another embodiment of a textile-based electrode system is represented with the aid of FIGS. 3A and 3B. In FIG. 3A a portion of a fabric 70, bounded by two horizontal axes, CC' and BB', is represented. A third horizontal axis, AA', placed equi-distant in a vertical direction from both CC' and BB', is also represented in FIG. 3A.

In FIGS. 3A and 3B, two textile-based electrodes are placed opposite one another in the horizontal direction. These electrodes include first and second outer portions of conductive yarns 30 and 30', as represented in FIG. 3A. These electrodes further include inner conductive yarn portions 34 and 34', represented in FIG. 3A, using dashed lines to illustrate the float yarns lying directly under yarn portions 30 and 30' respectively.

Similarly, FIG. 3A shows components of textile-based electrode systems, including third and forth outer portions of optional moisture retentive yarns, such as cotton, 46 and 46'. Such electrode systems further include inner conductive yarn portions 44 and 44', represented in FIG. 3A using dashed lines to illustrate the float yarns lying directly under conductive yarn portions 40 and 40' respectively. Conductive yarns 40 and 40', which are respectively continuous with 44 and 44', and surrounded by optional moisture retentive yarn portions 46 and 46', respectively.

Further represented in FIG. 3A, is a metallic connector 50 adapted to function as central point for electrical connection to a textile-based electrode.

FIG. 3B is a representation of fabric portion 70 after folding along horizontal axis AA' and causing axes CC' and BB' to meet co-linearly along a new horizontal axis CB-C'B'. As a result of making this fold in fabric portion 70 along horizontal axis M', a two-ply fabric portion is formed. The inner conductive yarn portions and the associated float yarn portions, respectively 34 and 44 and 34' and 44', are brought into physical contact (as represented in FIG. 3C) on an inner portion of the two-ply fabric portion.

Figure 3C:
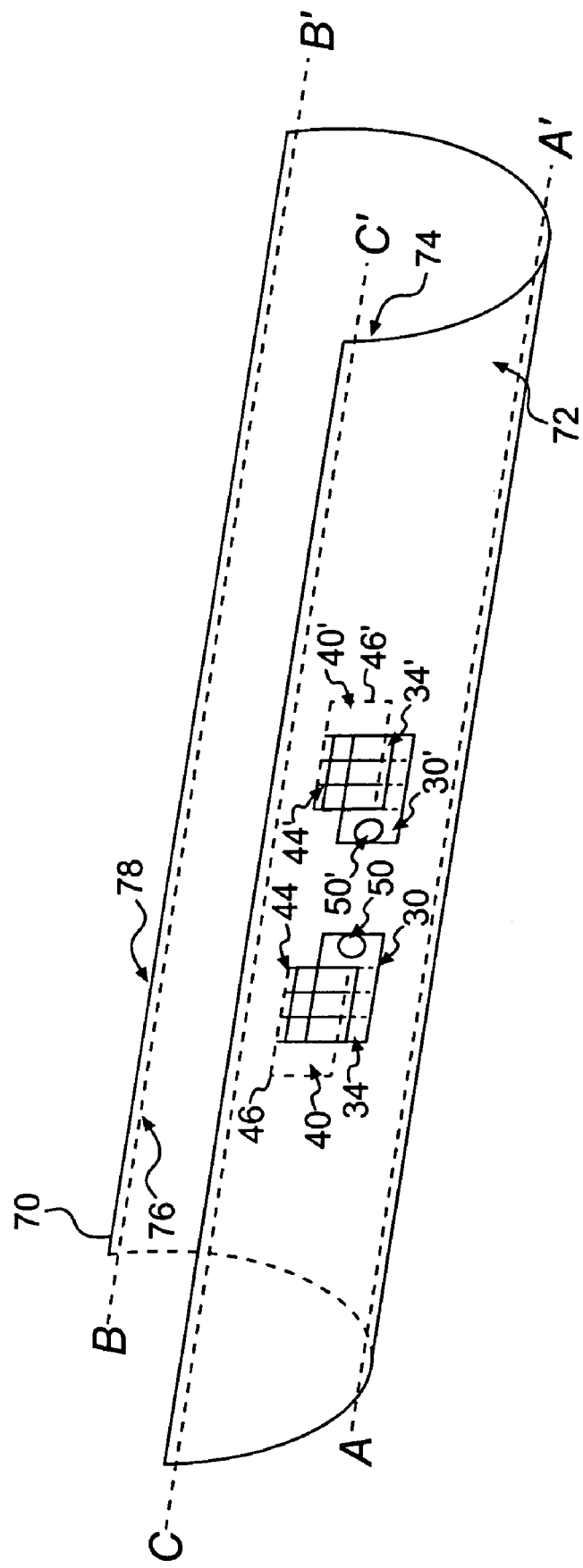

As represented by FIG. 3C, the conductive yarn portions 30 and 30' are on an outer surface portion 72 and the conductive float yarn portions 34 and 34' are on an inner surface portion 74 of the two-ply fabric. Similarly, as represented by FIG. 3C, the optional moisture retentive yarn portions 46 and 46', are on an outer surface portion 78 of the two-ply fabric. The conductive yarn portions 40 and 40' are on outer surface portion 78, float yarn portions 44 and 44', are all on an inner surface portion 76 of the two-ply fabric, as represented by FIG. 3C.

Referring now to FIG. 3C, the folded over fabric portion 70 is represented as having surface portions 78 and 72, as well as two textile-based electrodes, which are electrically continuous from surface portion 78 to surface portion 72. Such arrangement allows for the transmission and reception of electrical signals between surface portions 72 and 78. Connection points 50 and 50' can be adapted for sending or receiving such electrical signals.

Figure 4:
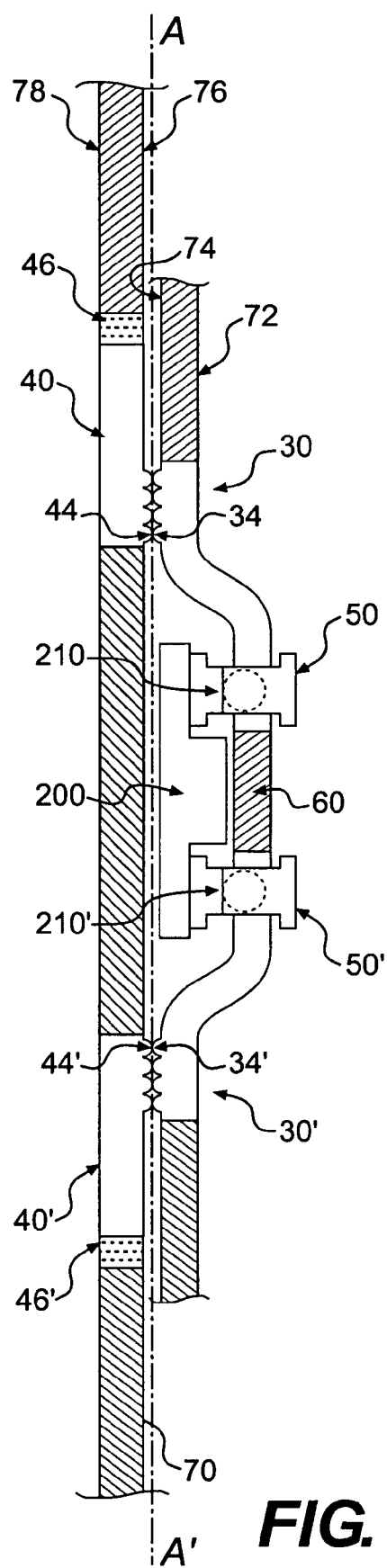
FIG. 4 is a schematic representation in partial cross-section of a pair of textile-based electrodes adapted to communicate with electronics capable of biophysical monitoring.

A means for adapting 50 and 50' for receiving and sending electrical signals is represented with the aid of FIG. 4. In this figure, fabric portion 70 is represented from a view between surfaces 74 and 76, which are facing one another as a result of folding 70 about horizontal axis AA' (as shown in FIG. 3B). Surface 78 (the side adapted to be in contact with a wearer's skin) contains conductive yarn portions 40 and 40' surface 72 contains conductive yarn portions 30 and 30'. Between surfaces 76 and 74, conductive float yarn portions 44 and 44' are brought into physical contact with conductive float yarn portions 34 and 34', thereby providing electrical continuity between conductive yarn portions 40 and 40' and conductive yarn portions 30 and 30'.

Electrically conductive contacts 50 and 50' are respectively attached to conductive yarn portions 30 and 30'. Electrically conductive contacts 50 and 50' may be made of any electrically conductive material, such as, for example, metallic conductors. Electrically conductive contacts 50 and 50' can be attached to conductive yarn portions 30 and 30' such that they communicate through 30 and 30' and are capable of contacting or engaging with electrically conductive contacts 210 and 210' respectively. Electrically conductive contacts 210 and 210' are associated with 200, an electrical device.

Electrical device 200 is represented in FIG. 4 as being placed between surfaces 74 and 76 of the folded over fabric portion 70. As a result, an electrical signal originating at conductive yarn portions 40 and 40' can be conducted directly to electrically conductive contacts 210 and 210' (as well as to 30 and 30'), respectively, which are each associated with electrical device 200. Alternatively, an electrical signal originating with electrical device 200 may be conducted directly to electrically conductive contacts 210 and 210' (as well as to 30 and 30'), and thereon to conductive yarn portions 40 and 40'.

An embodiment including optional yarns 60 is shown in FIG. 4, where the optional yarns 60 include, for example, PTFE filaments. The use of optional filaments 60 reduces the possibility of short circuiting of the textile-based electrodes in garments expected to be worn by heavily perspiring wearers. In one embodiment, the PTFE filaments can be wrapped about or twisted with LYCRA® brand spandex yarns. Otherwise, these yarns need no special preparation and can be readily integrated with the traditional textile filaments of the garment construction.

Figure 5:
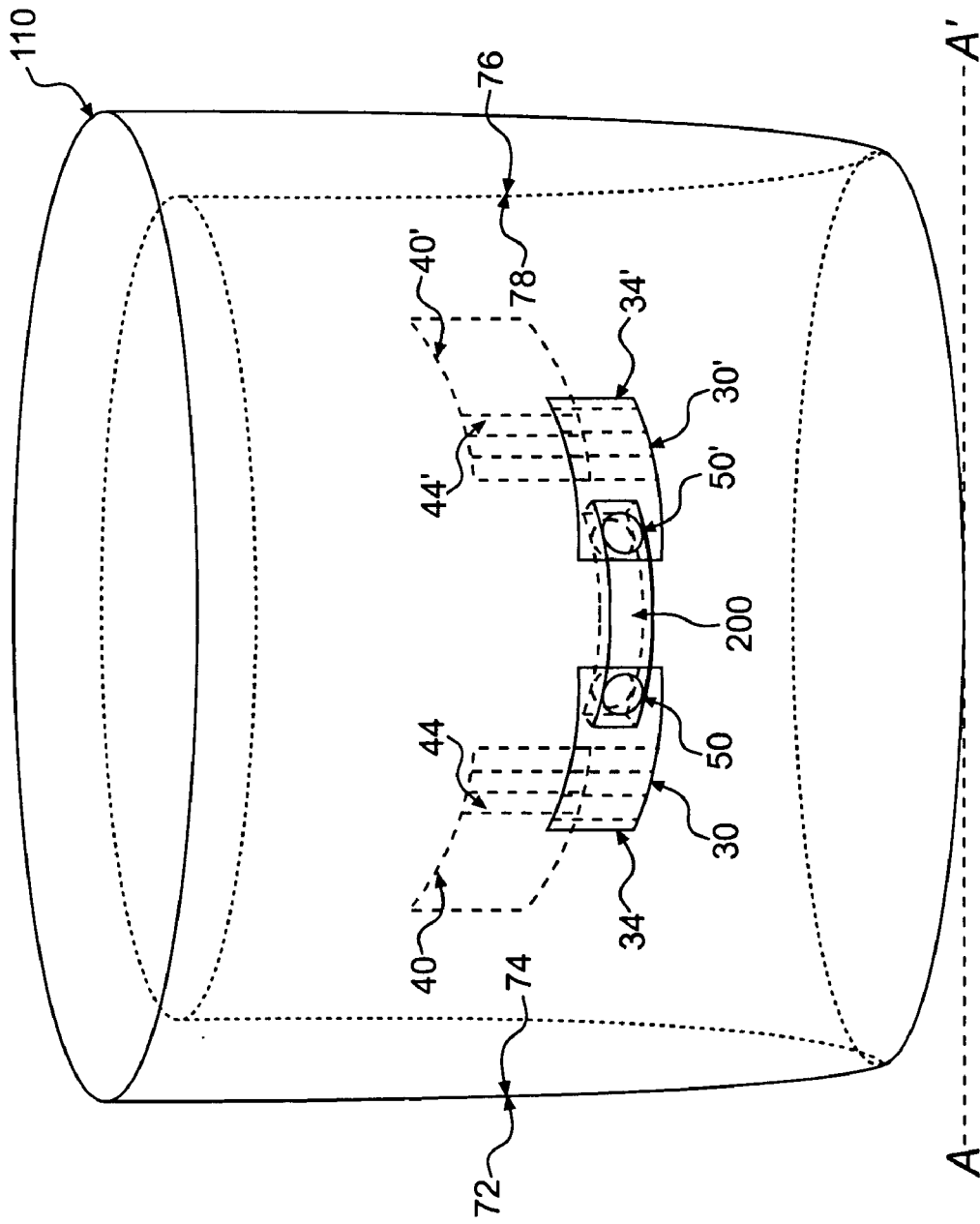
FIG. 5 is schematic representation of a continuous band adapted to wearing about the body and adapted for use with electronics capable of biophysical monitoring.

A portion of a wearable 110, fully integrated with two textile-based electrodes, is represented in FIG. 5. The wearable in FIG. 5 represents a sleeve, cuff, or band. In such an embodiment, the electrical device 200 is capable of receiving, storing, and/or transmitting certain biophysical parameters of a person or animal employing the wearable, fully integrated with textile-based electrodes.

As represented in FIG. 5, two textile-based electrodes can communicate directly with the electrical device 200, placed in a space formed between surfaces 72 and 74. The two conductive yarn portions 40 and 40' on the surface 78 are capable of contacting the skin of a wearer. As a result of skin contact with 40 and 40', any electrical signal originating from the wearer can be transmitted directly to 30 and 30' respectively, and, in turn, to electrical device 200, via the contacts 50 and 50'. Similarly, electrical device 200 may be capable of transmitting an electrical signal via contacts 50 and 50' and, in turn, through conductive yarns 30 and 30' and further in turn to conductive yarns 40 and 40', which contact the skin of the wearer and transmit the same signal to the wearer.

In another embodiment of the invention, the electrical device 200 is capable of biophysiological monitoring, such as sensing electrical signals associated with the electrical activity of the heart the wearer and thus the number of heart beats per unit time. The electrical device 200 can be engagable with contacts 50 and 50', as represented in FIG. 4, using conductive contacts 210 and 210'. The snap-engaged contacts 50 and 50' suitable for this application can, for example, be 11 mm contacts, available from PRYM NEWEY Textiles Group, Whitecroft, Lydney, Gloucestershire, UK. Reinforcement fabrics can be provided under each snap 50, 50', for example, in the form of a woven piece of CORDURA/COOLMAX®. These can serve to reduce the wear and eventual failure of the snaps located in the textile electrodes 30 and 30'.

The wearable 110 in FIG. 5 is in the form of a band that surrounds the mid-thorax of the wearer (can also be placed at other parts of the body e.g. wrist, arm, waist, etc.). The surface 78 of 110 is positioned toward the wearer's body and conductive yarn portions 40' and 40 are positioned horizontally so as to receive electrical signals associated with the electrical activity of a beating heart.

Optionally, the signal pickup from the wearer's skin may be further enabled using a portion of yarn, such as cotton yarn 46, 46' in FIG. 4, knitted into the fabric band portion surrounding 40 and 40'. Cotton yarns are known to be hydrophilic (as are, for example, silk, viscose, acetace an wool) and can promote the retention of body derived moisture in the vicinity of 40 and 40'.

It is also an option to provide a coating on or around the borders of the skin contacting electrodes 40 and 40', which helps promote sweating, thus allowing moisture to build up immediately after donning the wearable 110. Such coating may, for example, be desirable in applications where a wearer is not engaged in strenuous activity (in other applications, for example, where the wearer would be expected to be engaged in more strenuous activity, such coating may be less desirable). Suitable coatings include, for example, LYCRA® T162C polymer solution (from INVISTA™ Technologies S. á. r. l., Wilmington, Del. 19808) and ELASTO-SIL R plus 573 electrically conductive silicone rubber (from Wacker Silicones, WACKER-CHEMIE GmbH, Germany).

A suitable electrical device to demonstrate the function of the heart rate monitor embodiment is made by POLAR Electro Oy, Professorintie 5, Finland, 90440 Kempele; and designated as S810i™. The POLAR S810i™ includes an electronics module (200 in the embodiment represented by FIG. 5) and a wrist worn device that communicates via radio frequency with the module. The wrist worn device logs the data of the wearer. Data can be obtained during the wearer's activities, including, for example, strenuous activity like running, cycling, or skiing.

This embodiment of the invention can be superior to other means to wear a device such as the POLAR S810i™ since there is the capability to fully integrate the device using textile-based electrodes with a full fashioned garment. By comparison, chest worn belts and straps known for use with the POLAR S810i™ are not as form fitting, comfortable, and unobtrusive. The provision of a garment, such as a knitted top or a sports bra, fully integrated for biophysiological monitoring, can lead to a superior performing wearable embodiment of the invention.

Examples of wearables that can incorporate textile-based electrodes according to embodiments of the present invention include any type of a garment, including any type of a sports or athletic garment. Specific examples of garments include shirts, tank tops, bras, and underwear. However, it is important to note that the wearable can also include bands, straps, belts, or any other form of wearable article. A one layer electrode patch 40 can also be cut/sewn onto any wearable article.

Test Methods

In order to test the suitability of an embodiment falling within the scope of the present invention for use in biophysiological monitoring, the electrical conductivity between conductive textile yarns and any signal pickup point (such as 50, 50') must be established. In the case of an inner electrode of conductive yarns (e.g. 40 and 40'), the resistance between them and signal pickup points 50, 50' is measured using a FLUKE 180 series digital multimeter (from Fluke Electronics). In practice, a band of knit fabric, such as 70 in FIG. 5, is placed on a mannequin the resistance measured.

Short circuits between the textile electrodes, due to sweating of the wearer, is measured using a mannequin as above and a wet band of knit fabric 70. The wetting agent used to wet the fabric is a 1% aqueous NaCl solution, which approximates the ionic conductivity of human sweat secretions.

Figure 6:
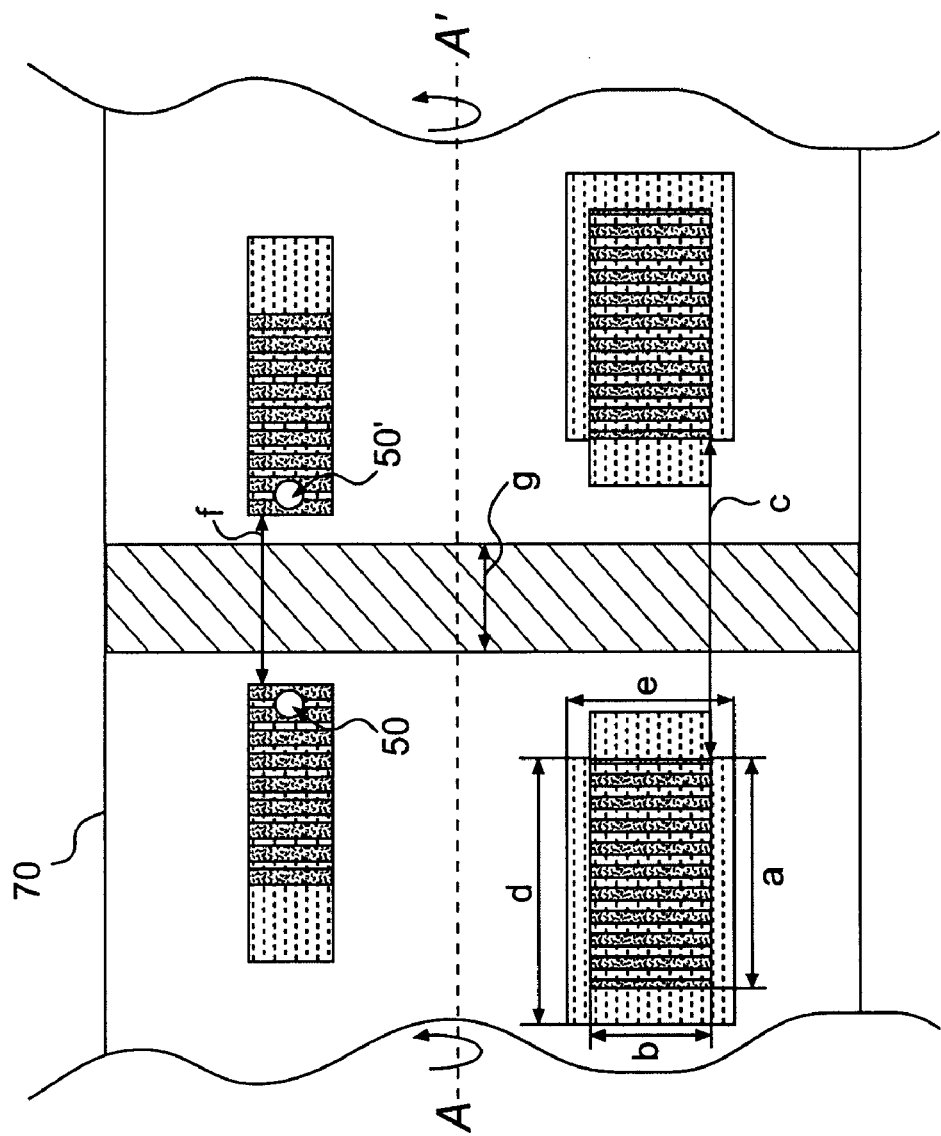
FIG. 6 is a schematic representation of a pair of textile-based electrodes and certain dimensions variable in their construction.

Represented in FIG. 6 are the dimensions a, b, c, d, e, f, and g of the textile-based electrodes of FIG. 5. The distance between the metallic pick-up points 50 and 50' is fixed at about 1.8 inches (46 mm) for each example.

Measurements of resistance are made between the textile electrodes 30 and 30', 40 and 40', and from among all textile electrodes and metallic pickup points 50 and 50'.

Comparison measurements of heart rate monitoring using the POLAR S810i™ electronics module and two different chest bands provided with the POLAR module (e.g. the POLAR hard and soft bands) provide a test of the quality of the signal pickup. In general, the POLAR S810i™ module is mounted in an upper chest worn knit fabric band (i.e., 70, as represented in FIG. 5) for this comparison test. During a session of strenuous exercise, heart rate data is logged according to the methods provided by POLAR with the S810i™ module and wrist worn data logger.

EXAMPLES

Examples of the invention were made in the form of heart rate monitoring belts (listed as 1-14 in Table 1). The heart rate monitoring belts were made by circular knitting using a SMA-8-TOP1 seamless, 13 inch body size, knitting machine from SANTONI (from GRUPPO LONATI, Italy) (hereinafter, "the SANTONI knitting machine"). In making the heart rate monitoring belts, a combination of different knitting constructions (including jersey and mock rib knit construction) using various types of yarns were used. In each example, the denoted electrode region was made using Xstatic® yarns of a silver metallized nylon yarn of 70 denier and 34 filaments from Laird Sauquoit Industries (Scranton, Pa., U.S.A. 18505) (hereinafter, "Xstatic® 70/34").

In each of heart rate monitoring belts 1-14, a base fabric was first constructed. The yarn used to knit the base fabric in each belt was Coolmax® 70/88 micro denier polyester yarn from INVISTA ("Coolmax®"), plated with Lycra® spandex (T-902C 260d). The Coolmax® and Lycra® spandex were knitted together using the SANTONI knitting machine at a ratio of about 92% Coolmax® and 8% Lycra® spandex (ratios of from about 75 to about 100% Coolmax® and from 0 to about 25% Lycra® spandex are also possible), wherein both plain jersey stitching and mock rib (1×1, 3×1, 2×1, 2×2) stitching were used in the regions of the fabric containing the textile-based electrodes (the "conductive regions"), as well as the non-conductive regions of the fabric.

For the regions of the fabric containing the textile-based electrodes (or "conductive regions"), a conducive yarn was knitted on one side of the base fabric (on the non-float regions) using the SANTONI knitting machine. The conductive yarn used in making heart rate monitoring belts 1-14 was X-static® 70/34 (although composite yarns form Bekaert having approximately 80% polyester and 20% stainless steel could also be used). In this regard, conductive regions represented by 40, 40', 30, and 30' (FIG. 3A) were knitted using plain jersey and mock rib stitch, and the conductive regions represented by 34, 34', 44, and 44' (FIG. 3A) were knitted using float stitches (regions 40 and 40' in FIG. 3A are also represented as having dimensions a×b in FIG. 6).

Metallic snaps (50 & 50' in FIG. 3A) were then installed to each of the heart rate monitoring belts 1-14 by first making small lead holes in the fabric (at positions 50 & 50' in FIG. 3A). Next, a snap reinforcement material having about a ½ inch diameter with a hole in the center (of about the same diameter as the corresponding small lead hole) was placed over positions 50 & 50', such that the holes in the fabric and the holes in the snap reinforcement material approximately overlapped. The snap reinforcement material was made of a plain weave of Cordura® nylon & Coolmax®. Snaps were then added by inserting part 1 of a female snap (e.g. PRYM-DRITZ 12 mm) through each hole, attaching part 2 of the corresponding snap on the other side of the fabric, and then riveting the snaps in place.

In the heart rate monitoring belts 1-14, the dimensions of regions 40 and 40' (FIG. 3A), i.e., a×b (FIG. 6), varied, as shown in Table 1. In addition, in the heart rate monitoring belts 1-14, the distance shown as width c in FIG. 6 varied, as shown in Table 1.

In heart rate monitoring belts 1 through 4, the snaps were placed such that electrically conductive contacts 210 and 210' in FIG. 4 were facing towards the skin (so that the electronic device 200 in FIG. 4 was outside the heart rate monitoring belt).

In heart rate monitoring belts 5 through 14, the snaps were placed such that electrically conductive contacts 210 and 210' in FIG. 4 were facing away from the skin (so that the electronic device 200 in FIG. 4 was inside the heart rate monitoring belt).

In addition, heart rate monitoring belts 11 through 14 included a hydrophilic yarn portion of cotton yarns (represented by dimensions d×e in FIG. 6) around each electrode portion (represented by dimensions a×b in FIG. 6). This hydrophilic yarn portion (shown as 46 and 46' in FIG. 3B) was knitted on to the opposite side of the fabric as the conductive regions (shown as 40 and 40' in FIG. 3A). The dimensions of d×e for heart rate monitoring belts 11 through 14 are shown in Table 1.

dation was also noted. A score of 10 was considered excellent and a score of 1 was considered poor. Where more than one score was reported, the measurement was a repeat measurement.

Table 1 provides a summary of heart rate monitoring belts 1-14 as well as Comparative Examples 1 and 2. The form of the heart rate monitoring belts was substantially as represented in FIG. 5.

TABLE 1

| Example No. | a × b *(inches) | C *(inches) | d × e *(inches) | g *(inches) | Resistance (ohms) | Wet Resistance (kOhms) | Signal Quality Rating |
|---|---|---|---|---|---|---|---|
| Comp 1 | 3.0 × 0.8 | 4.2 | N/A | N/A | 9 | N/A | 6 |
| Comp 2 | 2.8 × 0.6 | 4.0 | N/A | N/A | N/A | N/A | 7 |
| 1 | 3.3 × 0.7 | 4.9 | N/A | N/A | 4 | 4 | N/A |
| 2 | 3.3 × 0.7 | 5.5 | N/A | N/A | 4 | 4 | 6 |
| 3 | 3.3 × 0.7 | 5.4 | N/A | N/A | 5 | 4 | 3 |
| 4 | 3.3 × 0.7 | 5.7 | N/A | N/A | 9 | 4 | 5 |
| 5 | 3.3 × 0.7 | 4.2 | N/A | N/A | 8 | N/A | 6 |
| 6 | 3.3 × 0.7 | 4.2 | N/A | N/A | 8 | 6 | N/A |
| 7 | 3.3 × 0.7 | 4.6 | N/A | N/A | 6 | 3 | N/A |
| 8 | 3.3 × 0.7 | 4.7 | N/A | N/A | 6 | 2 | 3, 3 |
| 9 | 5 × 1.2 | 4.7 | N/A | N/A | 7 | 2 | N/A |
| 10 | 5 × 1.2 | 4.7 | N/A | N/A | 7 | 2 | N/A |
| 11 | 4 × 1.1 | 4.7 | 4.3 × 2.3 | N/A | 4 | 2 | 7, 8, **(3) |
| 12 | 4 × 1.1 | 4.0 | 4.3 × 2.3 | 0.7 | 3 | 7 | N/A |
| 13 | 3.5 × 0.9 | 4.0 | 3.8 × 1.8 | N/A | 4 | 2 | 7, 8, **(3) |
| 14 | 3.5 × 09 | 4.0 | 3.8 × 1.8 | 0.7 | 3 | 64 | N/A |

*[1 inch is equivalent to 25.4 mm]
**[repositioned electrode test]

Examples 12 and 14 of the invention also included a hydrophobic portion of yarns (represented as width g in FIG. 6). The material used in this hydrophobic portion was made up of about 90% PTFE 100d and about 10% Lycra® spandex and was knitted separately using a Lawson tube knitting machine (Made by Lawson-Hemphill Model # FAKSE). A band of this material was then cut and stitched in between the conductive regions, as shown in FIG. 6. The width of g for heart rate monitoring belts 12 and 14 is shown in Table 1.

Two fundamental measurements were made on the example heart rate monitor belts 1 through 14. These measurements included: (1) the dry resistance between skin contacting electrode portions (40 and 40') and the metallic snaps 50 and 50'; and (2) the water wetted (1% aqueous NaCl solution) resistance between the metallic snaps 50 and 50'.

For comparison purposes, the POLAR S810i "soft" belt was used for Comparative Example 1 and a POLAR S810i "hard" belt was used for Comparative Example 2. Each of these was tested along with the textile-based electrodes of the invention.

In the case of Comparative Example 1, the resistance was measured from the body contacting electrode to the snap which engaged the POLAR S810i module. This measurement was not made for Comparative Example 2 (as it is fully integrated).

The quality of signal pick-up was rated by a panel of experts in using the POLAR S810i. The signal quality of the POLAR belts was first rated for speed of first signal acquisition during the onset of a prescribed exercise routine for each wearer. The presence of noise or other signal degra-

What is claimed is:

1. A textile-based electrode system, comprising:
at least a first fabric portion and a second fabric portion;
wherein:
the first fabric portion comprises at least a first electrically conductive region;
the second fabric portion comprises at least a second electrically conductive region;
the first and second fabric portions are disposed in a partially overlying relationship;
the electrically conductive region of the first fabric portion and the electrically conductive region of the second fabric portion cooperate to provide a region of at least partial physical contact; and
the region of partial physical contact establishes electrical conduction between the first electrically conductive region and the second electrically conductive region.

2. The textile-based electrode system according to claim 1, wherein at least one of: (i) the electrically conductive region of the first fabric portion; and (ii) the electrically conductive region of the second fabric portion; comprises a float yarn.

3. The textile-based electrode system according to claim 2, wherein: (i) the electrically conductive region of the first fabric portion; and (ii) the electrically conductive region of the second fabric portion; both comprise float yarns that are stitched together.

4. The textile-based electrode system according to claim 1, wherein at least one of: (i) the electrically conductive region of the first fabric portion; and (ii) the electrically conductive region of the second fabric portion; comprises at least a portion of an elastified electrically conductive yarn.

5. The textile-based electrode system according to claim 1, wherein at least one of: (i) the electrically conductive region of the first fabric portion; and (ii) the electrically conductive region of the second fabric portion; comprises an elastic yarn at least partially plated with a conductive yarn.

6. The textile-based electrode system according to claim 1, wherein at least one of: (i) the electrically conductive region of the first fabric portion; and (ii) the electrically conductive region of the second fabric portion; comprises a fabric having a textured or ribbed construction.

7. The textile-based electrode system according to claim 1, wherein at least one of: (i) the electrically conductive region of the first fabric portion; and (ii) the electrically conductive region of the second fabric portion; further comprises at least a portion including a hydrophilic material.

8. The textile-based electrode system according to claim 1, wherein at least one hydrophobic material is incorporated into an electrically conductive region of either the first fabric portion or the second fabric portion.

9. The textile-based electrode system according to claim 1, further comprising means for transferring signals from at least one of the electrically conductive regions to a measuring device.

10. The textile-based electrode system according to claim 9, wherein the measuring device is attached to at least one of the fabric portions.

11. The textile-based electrode system according to claim 10, wherein a snap engagement attaches the measuring device to at least one of the fabric portions.

12. The textile-based electrode system according to claim 11, wherein said snap engagement is attached to at least one fabric portion and reinforced with a reinforcement material attached to said at least one fabric portion.

13. The textile-based electrode system according to claim 11, where the measuring device is placed such that snaps used in the snap engagement are adapted for facing away from the skin.

14. The textile-based electrode system according to claim 11, where the measuring device is placed such that snaps used in the snap engagement are adapted for facing towards the skin.

15. The textile-based electrode system according to claim 9, wherein the measuring device is a heart rate monitor.

16. The textile-based electrode system according to claim 1, further comprising a coating of polymer solution on and/or around the electrically conductive regions of the first fabric portion and the second fabric portion of the textile-based electrode system.

* * * * *